United States Patent [19]
Martin et al.

[11] Patent Number: 5,122,453
[45] Date of Patent: Jun. 16, 1992

[54] METHOD FOR DISCRIMINATING SURFACE STAINED LYMPHOCYTES

[75] Inventors: Grace E. Martin, Tarrytown; Robert J. Kanter, Old Bethpage; Young R. Kim, Hartsdale; Leonard Ornstein, White Plains; Hudson R. Ansley, Warwick, all of N.Y.

[73] Assignee: Technicon Instruments Corporation, Tarrytown, N.Y.

[21] Appl. No.: 188,803

[22] Filed: May 3, 1988

Related U.S. Application Data

[63] Continuation of Ser. No. 9,856, Feb. 2, 1987, abandoned, which is a continuation of Ser. No. 594,077, Mar. 28, 1984, abandoned.

[51] Int. Cl.$^5$ .................................... G01N 33/53
[52] U.S. Cl. ............................ 435/7.24; 435/21; 435/28; 435/29; 435/7.2; 435/7.21; 435/7.5; 435/7.9; 436/63; 436/166; 436/172; 436/519; 436/521; 436/532; 436/548; 436/805; 436/825
[58] Field of Search ............... 435/7, 21, 28, 29, 7.1, 435/7.2, 7.21, 7.24, 7.5, 7.9; 436/63, 166, 172, 519, 521, 532, 548, 805, 825

[56] References Cited

U.S. PATENT DOCUMENTS

| | | | |
|---|---|---|---|
| 4,228,237 | 10/1980 | Hevey et al. | 436/518 |
| 4,492,752 | 1/1985 | Hoffman et al. | 436/805 |
| 4,499,183 | 2/1985 | Sujansky et al. | 436/805 |
| 4,654,312 | 3/1987 | Chang et al. | 436/519 |

OTHER PUBLICATIONS

Reyes et al, "The surface morphology of human B lymphocytes as revealed by immunoelectronmicroscopy", *J. Exp. Med.* 1975; 141:393–410.
Schmitt et al, "Ultrastructural identification of human tonsil T–lymphocytes by peroxidase–conjugated anti–HTLA serum", *Experientia*, 1976; 32:1208–1210.
Brown et al., "The Distribution of HLA on human lymphoid, bone marrow and peripheral cells", *Eur. J. Immunol.*, 1979; 9:272–275.
Hofman et al, "Cytoplasmic as opposed to surface a antigens expressed on lumen peripheral blood lymphocytes and monocytes", *Clin Exp Immunol*, 1982; 49:355–363.
Falini, B. et al, "New Developments in Immunoperoxidase Techniques and Their Applications" Arch Path Lab Med, vol. 107, Mar. 1983, pp. 105–117.
Farr, A. et al, "Immunohistochemistry with Enzyme Labeled Antibodies: A Brief Review", J. of Immunol. Met. vol. 47, 1981, pp. 129–144.

*Primary Examiner*—Esther L. Kepplinger
*Assistant Examiner*—Carol A. Spiegel
*Attorney, Agent, or Firm*—Jeffrey M. Greenman

[57] ABSTRACT

A flow cytometry method for reproducibly detecting and counting a lymphocyte population of interest in a leukocyte suspension or whole blood sample in which the red cells are subsequently lysed. The suspension (or sample) is combined with a reagent comprising a primary antibody, either native, carrying an attached enzyme or biotin or other label, and a fixative reagent, in either order. Where the enzyme is not attached, an enzyme is coupled specifically to the primary antibody. The fixed suspension is reacted with a color-producing enzyme-cytochemical reagent. The suspension, now including stained and unstained fixed cells, is passed through a flow cytometer and the cells are characterized and counted on the basis of their light-scattering and light-absorbing properties.

30 Claims, 5 Drawing Sheets

METHOD FOR DISCRIMINATING SURFACE STAINED LYMPHOCYTES

This application is a continuation of U.S. application Ser. No. 07/009,856 filed Feb. 2, 1987, now abandoned, which is a continuation of U.S. application Ser. No. 06/594,077 filed on Mar. 28, 1984, now abandoned.

FIELD OF THE INVENTION

This invention relates to the field of flow cytometry, particularly to the use of specific binding assays in flow cytometry systems. Various specific binding assay protocols have been applied to the determination of substances in fluids, particularly body fluids, for many years. Flow cytometry instrument systems have been available for several years and are used in a variety of determinations, especially hematology and cellular immunology Background of the Invention All animal and plant cells are equipped with a large variety of protein enzymes which chemically catalyze the various biochemical reactions that are necessary for maintenance, growth and specialized cell functions Among these enzymes are subsets which are present in only a few, or even only one kind of cell.

Gomori, *Proc. Soc. Exp. Biol. Med.*, 42:23 (1939) and independently Takamatsu, *Trans Soc. Path. Japan*, 4:277 (1939) first described enzyme-cytochemistry when they realized that if an appropriate substance or combination of substances were introduced into a cell where there existed an enzyme that could produce a light-absorbing and insoluble product from that substance or those substances, all cells which contained that enzyme would become selectively colored (or dark) and could easily be distinguished from all other cells which lacked that enzyme by observing such cells with a light microscope. The introduced substances are natural or synthetic substrates for a specific enzyme which, after reaction with that enzyme, either spontaneously becomes light-absorbing and insoluble or become so because of reaction with other introduced reagent substances.

For such methodology to work with live cells, usually the introduced substances must (a) be able to enter the cell; (b) must not be toxic to the cell; (c) must convert to an extremely insoluble form; and (d) the conversion must occur extremely rapidly Cells are typically a few to tens of micrometers in diameter Molecules in aqueous solution typically diffuse such distances in fractions of seconds or seconds Therefore, if, after enzymatic reaction, the conversion to the insoluble form is delayed, it will deposit far from the enzyme and even outside of the cell. Since the product concentration diminishes with the cube of the distance it diffuses from site of reaction, its solubility product might not be exceeded at even short distances from the enzymatic site and, therefore, the cell remains unstained unless the product is extremely insoluble.

It has been especially difficult to simultaneously satisfy all of these criteria for live cells, particularly the combination of the permeability and toxicity criteria. For at least this reason, most enzyme-cytochemical methods have been applied to dead cells. In order to be able to distinguish one cell from another, whether stained or unstained, it is important to preserve a modicum of each cell's original external shape and internal structures. For this purpose, various histological and cytological fixing reagents (fixatives) are used which, to various degrees, insolubilize the proteins, nucleic acids and polysaccharide polymers of which cells are constructed. Fixing reagents which are used prior to enzyme-cytochemical staining must not destroy the catalytic chemical activity of the enzyme to be studied. See, Davis, et al., *J. Histochem. and Cytochem.*, 7:291 (1959).

Even for fixed cells, where the permeability and toxicity criteria are usually relaxed, it has, nonetheless, been extraordinarily difficult to satisfy, simultaneously, the remaining criteria.

Early enzyme-cytochemical methods, such as those described above, were therefore characterized by staining patterns which were so poorly localized that staining products often precipitated outside as well as inside the cell which originally contained the specific enzyme. A good deal of research effort of cytochemists in the ensuing years has been to develop methods with extremely high rates of conversion of the substrate plus extreme insolubility of the converted (usually colored) product. Methods which cleanly deposit product within a few nanometers of the enzyme are now known. The first truly high resolution dye-based enzyme-cytochemical staining techniques were first reported by Holt and O'Sullivan, *Proc. Roy. Soc. B.*, 148:465 (1958); Davis and Ornstein, *J. Histochem. and Cytochem.*, 7:297 (1959); Davis, *Proc. Soc. Exp. Biol. Med.*, 101:90 (1959); Davis, et al., *J. Histochem. and Cytochem.*, 7:291 (1959); and Lehrer and Ornstein, *J. Biophys. and Biochem. Cytol.*, 6:399 (1959).

Specific binding assay techniques have provided extremely useful analytical methods for determining various organic substances of diagnostic, medical, environmental and industrial importance which appear in liquid media at very low concentrations. Specific binding assays are based on the specific interaction between a ligand, i.e., a bindable analyte under determination, and a binding partner therefor. Where one of the ligand and its binding partner is a hapten or antigen and the other is a corresponding antibody, the assay is known as an immunoassay.

Enzymes are among the many labels which are commonly used in the form of a conjugate in which the enzyme is linked to the binding protein with a low molecular weight ligand with a species like that under assay or its binding partner. A substrate is included and reacts with the enzyme, to the extent permitted by the binding partner interaction, to provide a detectable response In immuno-enzyme-cytochemical staining methods, the very high chemical specificity of antibodies to bind selectively to unique molecular sites which are present on or in special subsets of cells is utilized. Such antibodies are either directly, or indirectly attached to enzymes for which high-resolution enzyme-cytochemical methods exist (e.g., peroxidase enzymes, alkaline phosphatase enzymes, etc.). When such an antibody and enzyme are appropriately attached to their target cell, the preparation can then be stained by an appropriate enzyme-cytochemical method, and only the labeled cells will accumulate light-absorbing (colored) product on or in them. Such methods are now widely used When fixing reagents are used prior to reaction with the cell-specific antibody, it is essential that they do not destroy the antibody-binding sites of the cells to be studied.

One of the classes of enzyme-labeled specific binding techniques used in immunocytology is referred to as the "immunoperoxidase" method, for which there are five basic protocols. Among the following methods, those which bind larger numbers of peroxidase molecules for each molecule of primary antibody bound increase sensitivity by "enzyme amplification". First, in the "direct conjugate" protocol, a peroxidase-antibody conjugate bins directly to a tissue antigen. Second, in the "indirect conjugate" protocol a primary antibody binds the tissue antigen and is, in turn, bound by a peroxidase-secondary antibody (anti-primary antibody) conjugate. Third, the "labeled antigen" protocol is essentially a sandwich technique in which primary antibody binds to both the tissue antigen and to an analogous antigen which has been conjugated with peroxidase Fourth, in the "enzyme bridge" protocol, primary and secondary antibodies are bound as described above and the secondary antibody is bound by a third antibody which has been conjugated with peroxidase. Fifth, the "peroxidase-antiperoxidase" protocol is as described for the enzyme bridge protocol with the addition that the peroxidase-tertiary antibody is followed by an anti-peroxidase antibody and excess peroxidase. In each protocol, hydrogen peroxide and a redox chromogen are introduced to exhibit the extent of available or localized peroxidase by enzyme-cytochemical staining and, thus, tissue specific antigen. See, generally, Falini, et al., *Arch. Pathol. Lab Med.*, 107:105 (1983).

Avidin is a glycoprotein, molecular weight 68,000, with four binding sites that have high affinity for biotin, one of the B vitamin complex. This high affinity binding has been used as an alternative to the labeled antibody methods described above in immunohistology. In the simplest protocol, a biotin-primary-antibody conjugate binds directly to a cellular antigen and is, in turn, bound by an avidin-peroxidase conjugate. In another protocol, the tissue-bound biotinylated primary antibody is bound with unlabeled avidin which, in turn, is bound with peroxidase-labeled biotin. The third such protocol uses an unconjugated primary antibody, a biotinylated secondary antibody and an avidin-biotin-peroxidase complex, from which it derives its connotation as the "ABC method". See, generally, Falini, et al., supra and Guesdon, J-L, et al., *J. Histochem Cytochem*, 27:1131–1139 (1979).

One example of the above is described in Hsu, S-M, et al., *J. Histochem. Cytochem.*, 29:577–580 (1981) which relates particularly to the use of the ABC method to identify antigens in formalin-fixed tissues. Assays were manually performed on formalin-fixed, paraffin-embedded thyroids. Serial sections were cut, deparaffinized, and processed through alcohol to water, as in routine tissue processing. The sections were processed by the "ABC" method and the final staining reactions were achieved by incubating the sections with aqueous hydrogen peroxide and diaminobenzidine tetrahydrochloride.

Human white blood cells can be classified as monocytes, polymorphonucleocytes (PMNs) and lymphocytes. There are two principal classes of lymphocytes. The first of these (the thymus-derived cell or T-cell) is immunologically active in effecting cell-mediated responses and the second (the bone marrow derived cell or B cell) is immunologically active in producing antibodies It is now recognized that T cells are divided into at least several subtypes, termed "helper", "suppressor", and "killer" T cells, which have the function of (respectively) promoting a reaction, suppressing a reaction, or killing (lysing) foreign cells. Lymphocyte subclasses of clinical interest are not easily distinguishable by other than immunological methods. The antigen on the outer surfaces of these lymphocytes are distinguishable with specific antibodies. It is particularly important to recognize and understand that a number of these antigens have been found to be remarkably fragile in the sense that mild chemical or physical treatment of the cell can either destroy the antibody-combining site and/or detach the antigen from the cell surface.

When lymphocytes are stained by immuno-enzyme-cyto-chemical methods with the cells in liquid suspension, they have typically been stained live, with high resolution methods. These produce a fine stippling of colored product on the outer cell surface. This distribution of product is due to the fact that the insoluble colored product precipitates within a few nanometers of the enzyme molecules (which are all on the outside surface of the cell). Half or more of the product diffuses away from the cell. When this diffused product precipitates, it is mostly freely suspended in the aqueous medium and drifts or is washed away from the cell. The other part diffuses towards the cell and either precipitates between and among the antibody and antigen molecules on the surface of the cell and is trapped in that network, or precipitates on or in the cell membrane, or, if the membrane is permeable to the product, just inside the cell.

Such surface-stippled cells absorb much less light than cells which have a similar amount of stain distributed more uniformly on or within the cells. Binet, et al., Blood Cells, 6:371–376 (1980) have examined such preparations by flow-cytometry (for instrumentation, see U.S. Pat. No. 3,740,143, assigned to a common assignee). Such surface-stippled cells generated too weak a signal to permit clean separation of the signals of the stained and unstained cells.

Also, it has been found that it is very difficult to get reproducible levels of such staining on duplicate samples of the same live lymphocytes, probably attributable to the variable damage to, and loss of the surface antigens of lymphocytes, and variable changes in permeability which can occur when live cells are manipulated by centrifugation, washing, etc., many times as is often required for such method. Therefore, it would appear that the low and variable staining levels can be in part attributed to the variable damage to, and losses from extensively manipulated live cells.

SUMMARY OF THE INVENTION

It is the purpose of this invention to both modify the treatment of lymphocytes as well as the composition of the enzyme-cytochemical reagent solution so that a highly reproducible response is obtained and a substantial quantity of the detectable enzyme product, which is initially produced on the outside surface of the cell, is precipitated on and/or in the cell to produce a large absorption signal which is easily resolved from the signals produced by unstained lymphocytes and other leukocytes in a flow cytometer.

The present invention provides a flow cytometry method of detecting a cell population of interest in a heterogeneous cell suspension. The method comprises individually and discretely combining the cell suspension with a reagent comprising a primary antibody specific for said cell population of interest and with a fixative reagent; coupling enzymes to the primary antibody with at least one ligand; thereafter combining said fixed cell suspension containing primary antibody bound cells of interest with at least one composition effective to detectably react therewith; passing the so-treated cell suspension, substantially a cell at a time, through an illuminating beam of optical radiation in a flow cytometer while measuring light scattered and absorbed by the cells passing therethrough; and differentiating cells of the population of interest based at least in part on measurement of the light scattered and adsorbed by those cells. The antibodies and other reagents used in the method can be combined with a cell sample in a continuous-flow system, as in U.S. Pat. No. 3,740,143, supra, or in a discrete reaction chamber at any point upstream of the point of illumination in the flow cytometer.

In accordance with the invention, it has been observed that use of this methodology for the automated determination of different populations, primarily of white blood cells, has the effect of causing larger quantities of the detectable form of the redox chromogen to be retained on the surface and/or in the cells of interest as distinguished from the surrounding medium. Better differentiation of cell populations is, therefore, made possible.

BRIEF DESCRIPTION OF THE DRAWINGS

Generally, FIGS. 1-11 illustrate the scattering-absorptive patterns in 2-dimensional plots of individual leukocytes in cell suspensions passed through a flow cytometer, each leukocyte being represented by a black dot.

DESCRIPTION OF THE PREFERRED EMBODIMENTS

The method of the invention is useful in that it permits the detectable species used to selectively and intensely color certain cells, particularly white blood cells, and not others. The cell sample can, for example, be whole blood or a heterogeneous white blood cell sample. The whole blood sample is preferably one in which the red blood cells have been lysed prior to introduction into the flow cytometer.

The terms "specific binding protein" as used herein refers to any substance, or class of substances, which has a specific binding affinity for the cell population of interest to the exclusion of other substances In the majority of embodiments, the present invention will incorporate specific binding assay reagents which interact with the sample in an immunochemical manner. That is, there will be an antigen-antibody or hapten-antibody relationship between reagents and/or antigens associated with the cells in the cell population of interest. Such assays therefore are termed immunoassays and the special interaction between the ligand and its receptor, or binding partner, is an immunochemical binding The use of either polyclonal or monoclonal antibodies is contemplated unless otherwise indicated. Additionally, it is well understood in the art that other binding interactions between the differentiating characteristics of the cell surface and a binding partner can serve as the basis of other specific binding assays.

The primary specific binding protein is usually an antibody which is specific for cell surface marker antigens. Such antigens are those which differentiate populations or subpopulations of white blood cells, tumor cells, or other heterogeneous cell samples within which it is useful to distinguish various groups. For example, several antibodies are known to be useful for the differentiation of lymphocyte classes and subclasses, including monoclonal antibodies from various hybridoma cell lines. Such include mouse monoclonal antibodies having designated specificities for all human T cells, suppressor T cells, helper T cells and the like. Other such antibodies are known for specific reactivity with human B cells.

In order to eliminate, or at least reduce the damage to, and losses from extensively manipulated live lymphocytes, we choose to fix the cells as early as is feasible. A fixative is chosen which insolubilizes and stiffens the cells without destroying the chemical activity of either the cell-specific surface antigen (when the fixing step precedes the application of the first antibody) or of the attached labels or exposed secondary immuno-reactive groups which are required for the subsequent steps of the method (when the fixing step follows application of the first antibody), and which does not cause the cells to adhere to one another or to the walls of the vessel in which they are contained. Monoaldehydes, such as formaldehyde, paraformaldehyde and acrolein, and di-aldehydes such as glutaraldehyde, used alone or in combination, have been found useful for cells in suspension. See, for example, U.S. Pat. Nos. 3,741,875 and 4,412,004, both assigned to a common assignee.

The secondary specific binding protein is usually an antibody against the class of proteins, usually immunoglobulins, of which the primary specific binding protein is a member. Thus, this secondary antibody reacts with and is specific for all antibodies of the primary antibody class In one preferred embodiment, the methodology also uses a reagent conjugate comprising an enzyme which is bound to an avidin molecule Another embodiment of this methodology uses a reagent conjugate comprising an enzyme bound to a biotin molecule which is in turn bound to an avidin molecule. Examples of enzymes suitable for such use include peroxidase (such as horseradish peroxidase), alkaline phosphatase and combinations of these and other enzymes.

The redox chromogen used is critical in that it must be insoluble in the reaction milieu in its reacted form. Those which have been identified as useful in the invention include 3-amino-9-ethylcarbazole and 4-chloro-1-napthol. Chromogens producing a product appreciably soluble in the reaction environment are not useful.

As previously noted in accordance with the invention, the primary antibody, biotinylated secondary antibody, labeled conjugate, enzyme substrate and redox chromogen can be combined with the cell sample under assay, either prior or subsequent to introducing said cell sample to a flow cytometer in which the method is to be performed.

It is preferred to introduce the cell sample into a fluid stream flowing in a conduit or analysis channel in the flow cytometer. This preferably comprises establishing a flowing stream of a flowing fluid sheath stream in the conduit or analysis channel and thereafter introducing the said sample into the flowing fluid sheath stream. Such sheath streams are usually of fluids having a refractive index substantially identical to that of the cell sample suspending medium. One such flow cytometer which uses a sheath stream carrier fluid is used in the Technicon Hemalog D and H-6000 systems, which handle all routine hematology tests. Detailed information on the Hemalog D and H-6000 systems is available from Technicon Instruments Corporation, Tarrytown, N.Y.

In accordance with the invention, it has been observed that use of this methodology for the automated determination of different populations, primarily of lymphocytes, has the effect of causing the detectable form of the redox chromogen to inhabit and be retained by the lymphocyte population of interest as distinguished from the surrounding medium or the lymphocytes from the sample which are other than those for which the assay method is specific. Better differentiation of cell populations is therefore made possible.

Each of FIGS. 1-11 are 2-dimensional displays from the peroxidase channel of an H-6000 instrument system (Technicon Instruments Corporation, Tarrytown, N.Y.) in which absorption is measured along the abscissa and light scattered out of the forward direction is measured along the ordinate. Each dot represents the measured coordinates of a single cell. Three pre-set thresholds enable the operator to separate and count distinct clusters of signals. Absorption Low (AL) and Absorption High (AH) are shown as vertical lines Scatter Low (SL) is shown as a horizontal line. H-6000 gives separate counts for all signals above SL and to the left of AL, between AL and AH, and to the right of AH. It will ignore all the signals below SL, which represent signals smaller than those from cells, thus removing noise signals due to red cell ghosts, platelets, etc.

These lymphocyte-labeling methods are applied to either lymphocyte-enriched samples or whole blood samples. Whole blood contains both neutrophils and eosinophils (which are PMNs) and monocytes, all of which carry endogenous peroxidases. After peroxidase staining, distinguishing these cells from peroxidase-labeled lymphocytes could pose a problem As will be illustrated, because of the much greater intensity of staining of eosinophil, neutrophils and some monocytes, the signals from these cells are easily separated from the positive (peroxidase-labeled) lymphocytes by the AH threshold. The remaining weakly stained monocytes which lie between the AL and AH threshholds can be counted separately in the control, and subtracted from the count from between the AL and AH threshholds in the corresponding experimental run.

Also, it is usual for even the best lymphocyte-enriched samples to be contaminated with a few PMNs and monocytes. (See FIGS. 1-7.) Similar subtraction of appropriate controls correct for such contamination.

The following working examples describe experiments which were performed in developing the present invention. Standard, commercially available reagent grade chemicals were used whenever possible.

EXAMPLE I

Several experiments were performed in which the prior art was explored and illustrated with respect to detection and counting of lymphocyte subsets by means of immunoassays using a peroxidase indicator labeling system with flow cytometry in visible and near infrared light. Following the procedure described in the teaching of Binet, et al., supra, an "indirect conjugate" protocol was used in which the mouse monoclonal pan T-cell antibody, T101 (Hybritech, LaJolla, Ca.), was followed by a peroxidase-conjugated antimouse secondary antibody (Cappel, Cochranville, Pa.). The peroxidase enzyme thus associated with the surface of the T cells was stained by each of one of two different redox chromogens, namely, 3-amino-9-ethylcarbazole and 4-chloro-1-naphthol. The details of the methods employed are as follows:

Experiment A

Lymphocyte-enriched suspensions were prepared as described in Boyum, A., *Scand J. Clin. Lab. Invest.*, 21, Suppl. 97:77 (1968). The lymphocyte fraction was harvested and the cells washed three times by centrifuging for 10 minutes at 400 g in neutral phosphate buffered saline (PBS) containing 0.4% bovine serum albumin (PBS/BSA). The supernatant fluid was aspirated to waste. Sufficient PBS/BSA was added to the final harvest of cells to yield a concentration of 107 cells per ml. A 100 μl aliquot of this cell suspension was dispensed into a test tube. An equal volume (100 μl) of T101 at a strength of 10 μg/ml was added to the tube and incubated for 30 minutes at 4° C. The cells were then washed with PBS/BSA three times by centrifuging for 45 seconds at 100 g, discarding 99% of the supernatant fluid and retaining the cell pellet each time. The cell pellet was then resuspended in residual supernatant and 100 μl of secondary antibody conjugated with peroxidase (20 μl/ml) was added and incubated for one hour at 4° C. The wash procedure in PBS/BSA was repeated three times.

The cells were then resuspended and incubated for 10-20 minutes at room temperature in 1 ml of staining mixture consisting of: 2 mg 3-amino-9-ethylcarbazole (AEC) dissolved in 0.5 ml dimethylformamide (DMF) to which was added 9.5 ml 0.05 M acetate buffer (pH 5) plus 50 μl 3% $H_2O_2$.

A 1 ml volume of the suspension of cells in the staining mixture was then diluted with 2 ml PBS and the cells were introduced into the flow cell of an H-6000 flow cytometer, by-passing the manifold by disconnecting the sample line at the peristaltic pump leading to the flow cell of the peroxidase channel and placing the disconnected sample line directly into, and to the bottom of, the test tube containing the reacted cell suspension. The results are illustrated in FIG. 1.

Figure 3:
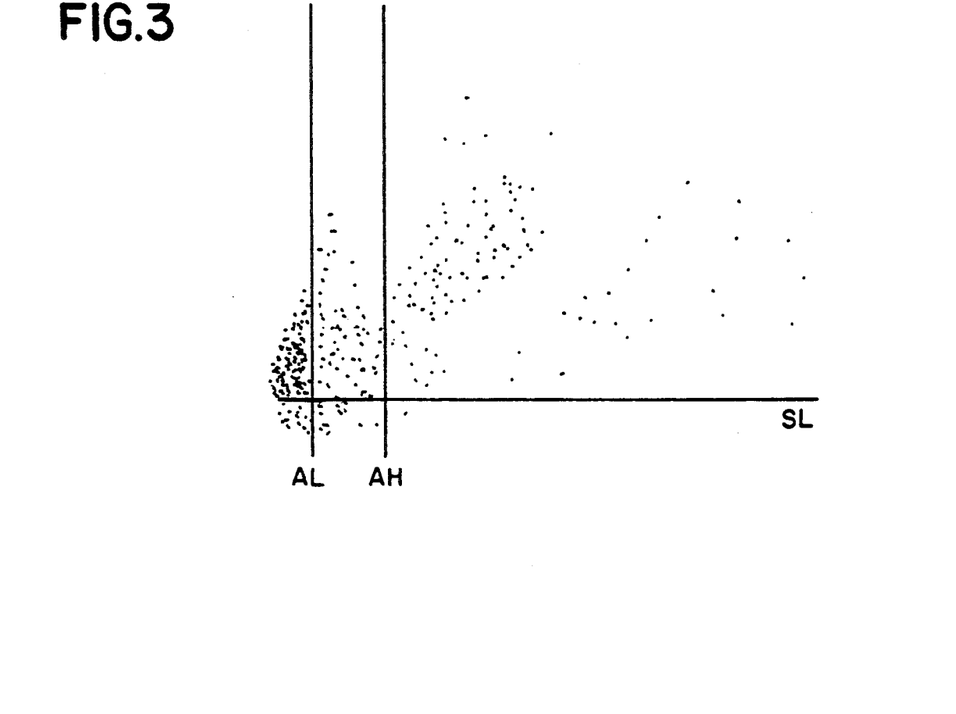
FIG. 3 is an unlabeled control for such prior art techniques.

A negative control was run in which every step was the same as described above except that the primary antibody was omitted. The results for the control are illustrated in FIG. 3. FIG. 3 (control), shows all lymphocytes to the left of AL. The dots between AL and AH are contaminating monocytes. The dots to the right of AH are contaminating neutrophils and eosinophils.

Figure 1:
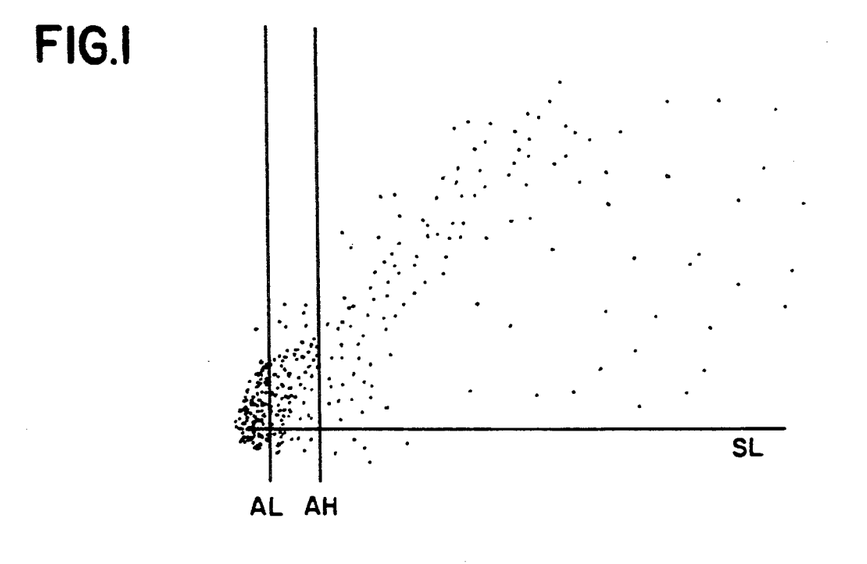
FIGS. 1, 2 and 4 illustrate results obtained using prior art techniques for processing unfixed leukocyte-enriched cell suspensions

In FIG. 1, the stained lymphocytes are distributed across AL and into the space between AL and AH. All other cells remain as in the control (FIG. 3). The staining is clearly inadequate to separate all of the stained lymphocytes from the unstained lymphocytes. This can be attributed, in part, to the variable damage to and losses from the cell surfaces following the extensive manipulation of these live cells.

Experiment B

Figure 2:
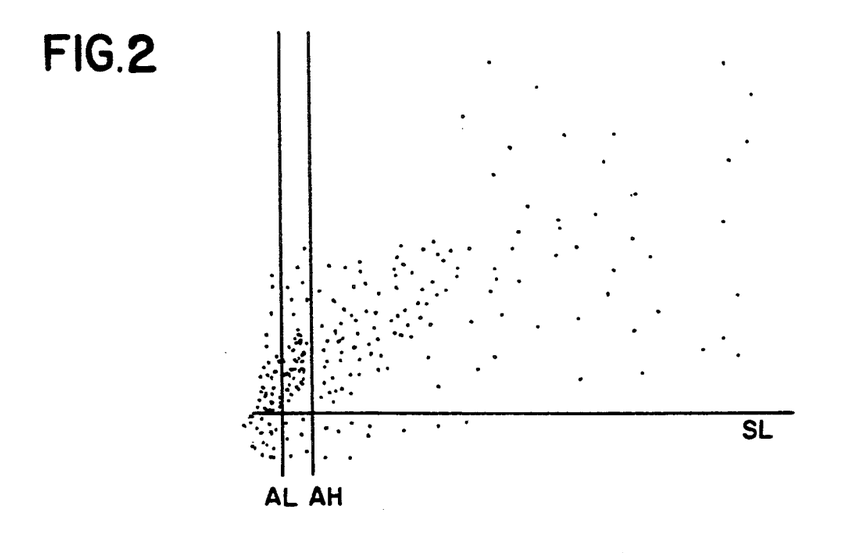

Next, exactly the same method as described in Experiment A was followed, except that 2 mg 4-chloro-1- naphthol was substituted in place of AEC in the staining mixture An attempt was made to conform to the published method although Binet, et al., do not give specific instructions on the details of their staining mixture containing the 4-chloro-1-naphthol. The results are illustrated in FIG. 2 and are comparable to those illustrated in FIG. 1, wherein the stained and unstained lymphocytes cannot be clearly distinguished. A negative control was run in which every step was the same as described above except that the primary antibody was omitted The results for the control are the same as are illustrated in FIG. 3.

Experiment C

Figure 4:
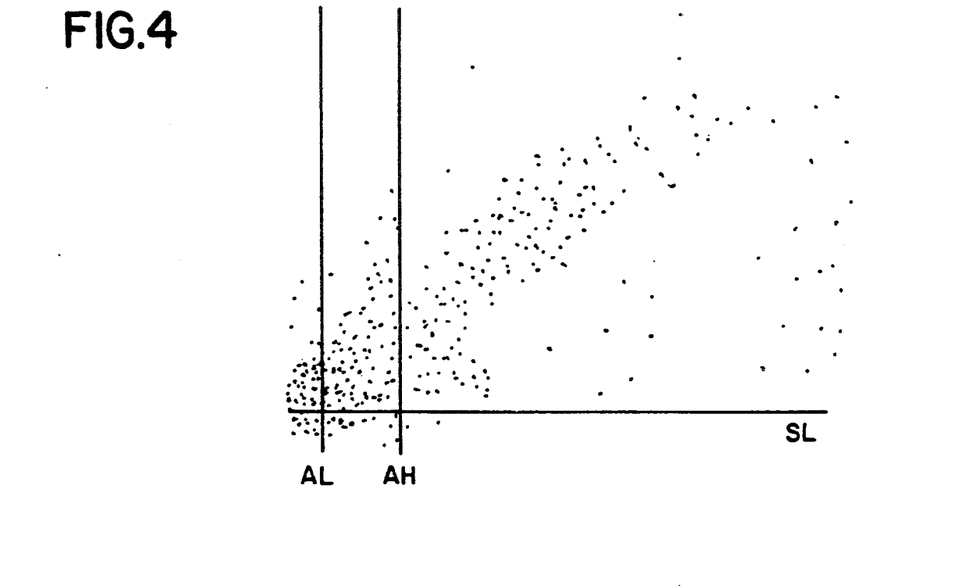

In this experiment, an "enzyme bridge" protocol, using unfixed cells and T101, was followed This protocol amplifies the amount of peroxidase bound and had not yet been tested in this kind of system at the time of Binet, et al. In this experiment all the steps were the same as in Experiment A except that, instead of peroxidase-conjugated secondary antibody, the remaining steps were the addition of a biotinylated secondary antibody followed by three PBS/BSA washes, followed by ABC complex, and three more PBS/BSA washes. Secondary antibody and ABC provided in a VectaStain Kit (Vector Laboratories, Burlingame, Ca.), were used in accordance with the manufacturer's instructions Although the staining is somewhat increased, as shown in FIG. 4, the stained and unstained lymphocytes still cannot be clearly distinguished, as was the case in FIGS. 1 and 2.

Experiment D

Binet, et al., sometimes fixed their cells after they had been completely processed (i.e., after staining step with AEC in Example I). Their procedure was to add 1 ml 0.7% formaldehyde to 1 ml of the AEC cell suspension, allowing the mixture to stand at room temperature for 10 minutes and diluting with 1 ml PBS before introduction into an H-6000 flow cell. The results were substantially identical to those illustrated in FIG. 1.

This example shows that the prior art was inadequate for lymphocyte differentiation even when combined with every known improvement in the art. There was no separation of positive and negative lymphocytes into distinct clusters and poor reproducibility was noted for all the attempts described here.

Further, this prior art is characterized by either no fixation or fixation very late in the procedure, long after the cells have been severely abused by the intervening processing steps and yielded inadequately stained cells.

EXAMPLE II

The experiments reported here compare "ABC" lymphocyte differentiation immunoassays using OKT3 (Ortho Diagnostics, Raritan, N.J.) or T101 (Hybritech, LaJolla, Ca.) as the primary antibody, again using a lymphocyte suspension prepared as described in the previous example In one experiment (Experiment A) a fixation step was performed after incubation with secondary antibody. In a second experiment (Experiment B) the same type of fixation was performed, in accordance with the invention, prior to incubation with secondary antibody. In a third experiment (Experiment C), the second experiment is repeated with T101.

Experiment A

A 100 $\mu$l aliquot (approximately $10^6$ cells) of a lymphocyte enriched suspension (as in Example I, Experiment A) was dispensed into a clean test tube. A 100 $\mu$l volume of phosphate buffered saline containing 0.4% bovine serum albumin (PBS/BSA) and 5 $\mu$l OKT3 (pan T primary antibody at a strength of 25 $\mu$g/ml, was added and incubated for 15 minutes at 4° C. One (1) ml of PBS/BSA containing 0.3% ethylene diamine tetracetic acid (EDTA) (PBS/BSA/EDTA) washing solution was added to the above and the mixture was centrifuged for 45 seconds in order to pellet the cells without pelleting an excessive number of platelets. 99% of the supernatant was aspirated to waste and this washing procedure (PBS/BSA/EDTA) repeated two more times. This yielded a pellet of washed lymphocytes including OKT3-bound cells.

These cells were then resuspended in residual supernatant and 100 $\mu$l of biotin-conjugated anti-mouse immunoglobulin antibody (Vector Labs, Burlingame, Ca.), diluted according to the Vector protocol, was added. The mixture was incubated for 15 minutes at 4° C. Again, three washes were performed with PBS/BSA/EDTA. This yielded a pellet of washed lymphocytes including OKT3/secondary antibody-biotin bound cells.

Then, after reaction with secondary antibody, the cells were resuspended in residual supernatant and 1.0 ml of 4.6% formaldehyde in 0.07 M PB was added and incubated for 10 minutes at 4° C. The mixture was washed as above three times. This yielded a pellet of washed formaldehyde-fixed lymphocytes including OKT3/secondary antibody-biotin bound cells.

Figure 5:
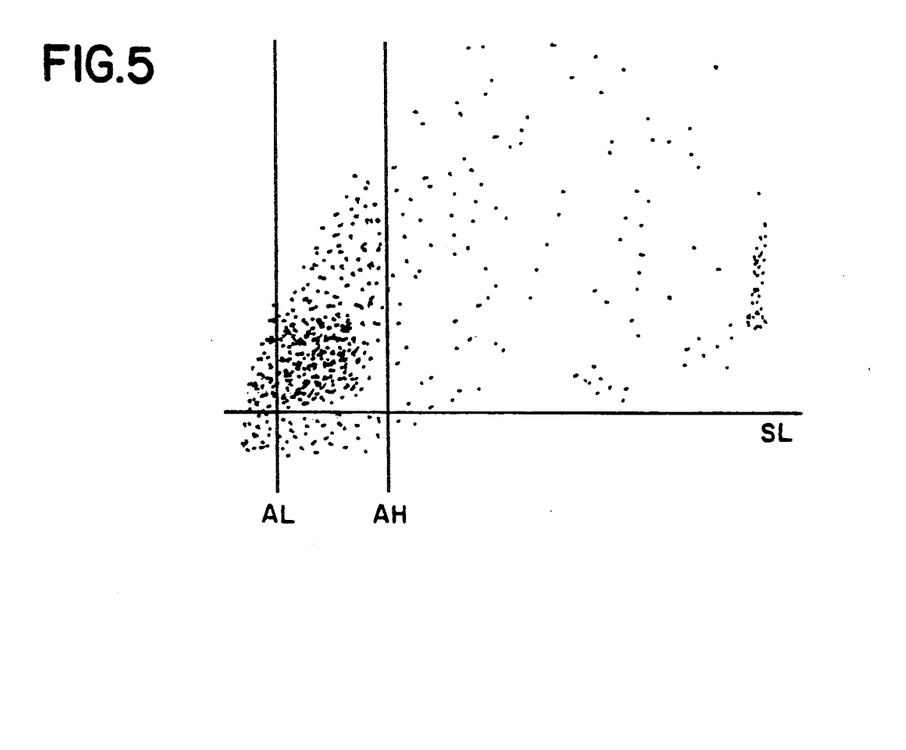
FIGS. 5 and 6 illustrate the results obtained when fixation of the cell suspension is effected after and before, respectively, the application of the second antibody to the leukocyte.
Figure 7:
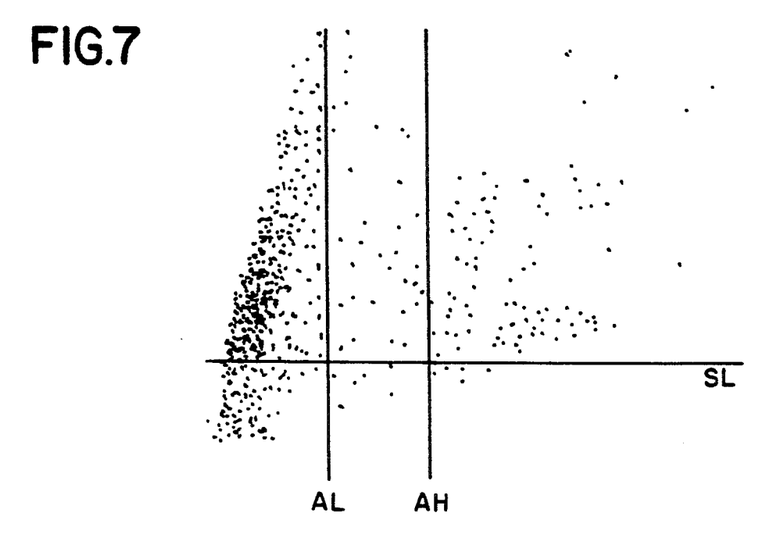
FIG. 7 is an unlabeled control for the processes depicted in FIGS. 5 and 6.
Figure 8:
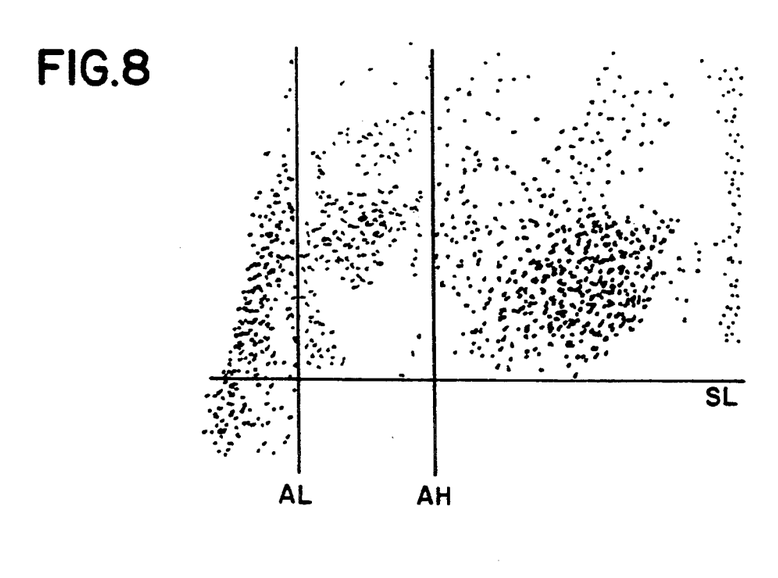
FIGS. 8 and 10 illustrate the results obtained according to the present invention when using whole blood, where cell fixation is effected immediately after and before, respectively, the application of the primary antibody to the leukocytes.

These cells were then resuspended in residual supernatant and incubated with 100 $\mu$l (90–190 $\mu$g ml) avidin-biotin-horseradish peroxidase complex (ABC) at 4° C. for 15 minutes. Again, three washes were performed using PBS/BSA/EDTA. This yielded a pellet containing fixed peroxidase-bearing cells. This pellet was resuspended in residual supernatant and a 1.0 ml aliquot of a staining solution was added The staining solution contained 8 mg 3-amino-9-ethylcarbazole (AEC) in 10 ml methanol combined with 100 $\mu$l 3% H made up to 25 ml using 0.05 M sodium acetate buffer (pH 5). After 10 minutes at room temperature, the mixture was combined with 2.0 ml PBS and aspirated directly through a sheathed H-6000 flow cell via a peristaltic pump to obtain the cell signatures in the peroxidase channel The result is illustrated in FIG. 5. A negative control was run in which every step was the same as described above except that the primary antibody was omitted. The results for the control are illustrated in FIG. 7.

Note that some separation between unstained lymphocytes (to the left of AL) and the stained lymphocytes (between AL and AH) has been achieved in this protocol which fixes the cells after reaction with this second antibody. Such separation is marginal.

Experiment B

A 100 $\mu$l aliquot of a lymphocyte-enriched suspension was treated as described in Experiment A to yield a pellet of washed lymphocytes including OKT3-bound cells.

These cells were then resuspended in residual supernatant and 1.0 ml of 4.6% formaldehyde in 0.07 M PB was added and incubated for 10 minutes at 4° C. The mixture was washed with PBS/BSA/EDTA three times. This yielded a pellet of washed, formaldehyde-fixed lymphocytes including fixed primary antibody (OKT3)-bound cells.

Figure 6:
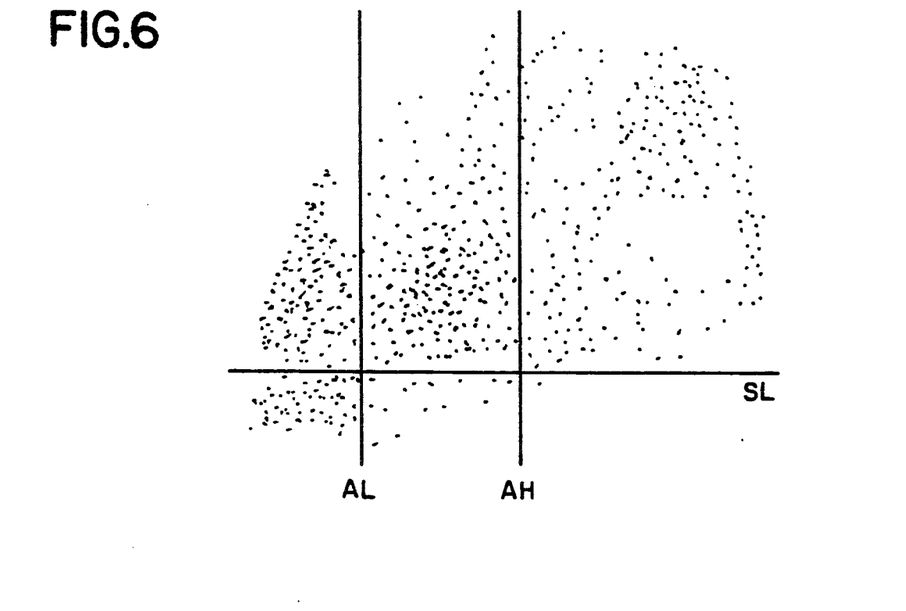

Then, these cells were reacted with biotin-conjugated anti-mouse immunoglobulin antibody, ABC complex, and the staining solution as described in Experiment A. After 10 minutes at room temperature, the mixture was combined with 2.0 ml PBS and fed into an H-6000 flow cytometer as described above. The result is illustrated in FIG. 6.

Experiment C

An experiment identical to experiment B was run, except that T101 was used instead of OKT3, as the primary antibody. The results were substantially the same as those obtained in Experiment B, FIG. 6.

Thus, Experiments A, B and C demonstrate that the labeled lymphocyte subset no longer forms a continuum with the unlabeled subset, as in Example 1, FIGS. 1, 2 and 4. Instead, the labeled subset forms a discrete cluster, separated from the unlabeled cluster by a gap. This gap is narrow in FIG. 5 (post-secondary-antibody fixation), but in FIG. 6 it is very wide (pre-secondary-antibody fixation), thus meeting the essential condition necessary for convenient and accurate counting and classifying of subsets of cells in flow cytometry. The width of the gap can be attributed to how early in the process the cells were fixed.

EXAMPLE III

As reported here, lymphocyte differentiation immunoassays were also performed in accordance with the invention on whole blood samples using OKT4 (Ortho Diagnostics, Raritan, N.J.) or Coulter Clone T4 (Coulter, Hialea, Fl.) as the primary antibody. In one experiment (Experiment A) a fixation step was performed after incubation with primary antibody (OKT4) but prior to incubation with secondary antibody. In a second experiment (Experiment B) the same type of fixation was performed prior to incubation with primary antibody (Coulter Clone T4).

Experiment A

A 100 μl aliquot of anticoagulated whole blood was dispensed into a clean test tube. This was mixed with 100 μl of cold isotonic buffered saline containing approximately 2.5 μg/ml OKT4 T-cell monoclonal antibody (Ortho Diagnostics, Raritan, N.J.) and the mixture was incubated at 4° C. for 15 to 30 minutes Red cells were then lysed by adding 2 ml of 0.85% NH$_4$Cl solution at room temperature with thorough mixing. The cell suspension was centrifuged for 1 minute (1,000 g) to harvest the white cells. The white cells were recovered and washed twice in PBS/BSA/EDTA at 4° C. This yielded a pellet of washed white blood cells.

Figure 9:
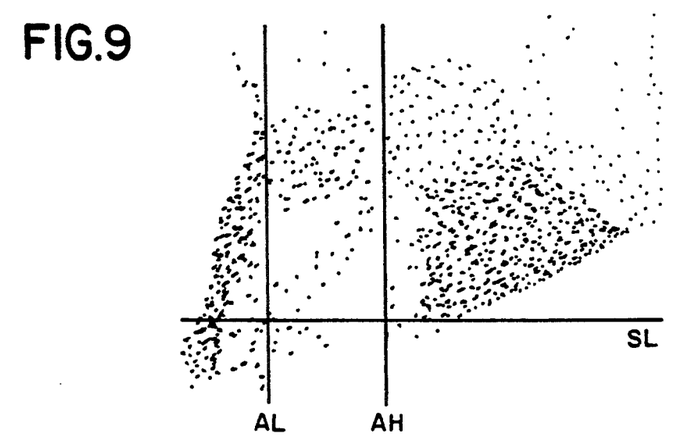
FIGS. 9 and 11 are unlabeled controls for FIGS. 8 and 10, respectively.
Figure 10:
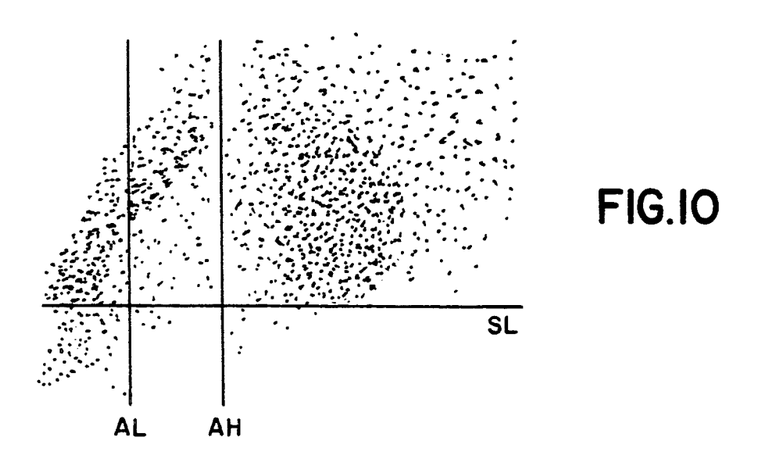

Then, these cells were resuspended in the residual supernatant and fixed by adding 1 ml of 0.075 M phosphate buffered 7.5% formaldehyde solution (pH 6.7) containing 15% dextrose. After 5-10 minutes, the fixed cells were washed twice with PBS/BSA/EDTA. Then, after fixation, the cells were resuspended in residual supernatant, incubated with 0.1 ml of biotinylated secondary anti-mouse immunoglobulin antibody (12.5 μg/ml) for 15-30 minutes at room temperature and were washed twice with PBS/BSA/EDTA. The washed cells were resuspended in residual supernatant and incubated with 0.1 ml avidin-horseradish peroxidase conjugate (A:HRP) in PBS (50-100 μg A:HRP per ml PBS). After 15-30 minutes at room temperature, the cells were washed three times with PBS/BSA/EDTA and mixed with 0.5 ml of a staining solution which contained 0.3 mg 4-chloro-1-naphthol, 16% ethanol, 0.01% H$_2$O$_2$ in 0.025 M phosphate buffer (pH 7.5) and incubated for 10 minutes at room temperature. The stained cell suspension was diluted to 1 ml with phosphate buffer and aspirated directly through the H-6000 flow cell as previously described, with the results illustrated in FIG. 8. A negative control was run in which every step was the same, as described above, except that the primary antibody was omitted. The results for the control are illustrated in FIG. 9.

Experiment B

A 100 μl aliquot of anti-coagulated whole blood was treated with 0.85% to lyse red cells, the white cells were harvested and washed twice with PBS/BSA/EDTA as described in Experiment A herein.

Figure 11:
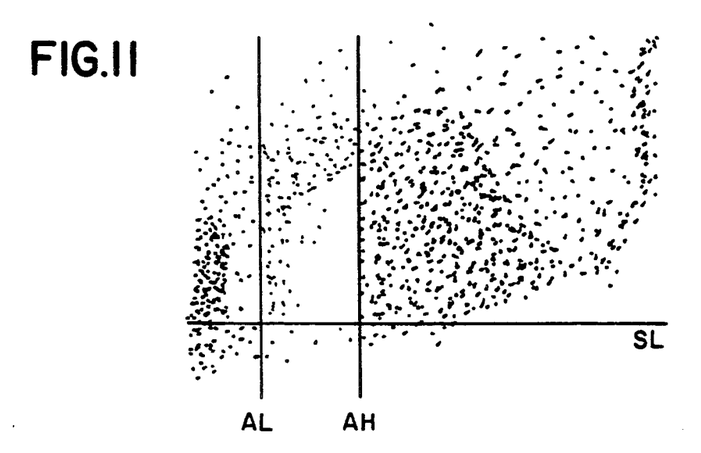

Then, the cells were fixed at room temperature by mixing the resuspended pellet with 1 ml of 0.075 M phosphate buffered 7.5% formaldehyde solution (pH 6.7), which contains 15% dextrose, for 5-10 minutes, and washed twice wit PBS/BSA/EDTA. The cell pellet was resuspended in residual supernatant, incubated with 0.2 ml of T4-biotinylated primary antibody solution (Coulter, Hialea, Fl.) in PBS, diluted from stock according to the manufacturer's directions, for 15-30 minutes at room temperature and washed twice with PBS/BSA/EDTA. The resulting pellet was resuspended and incubated with 0.1 ml avidin-peroxidase (50-100 μg/ml PBS) for 15-30 minutes at room temperature and washed twice with PBS/BSA/EDTA. The resulting pellet was resuspended, mixed with 0.5 ml of a staining solution which contained 0.3 mg 4-chloro-1-naphthol, 0.01% H$_2$O$_2$ and 16% ethanol (or methanol) in 0.025 M phosphate buffer (pH 7.5) and incubated for 10 minutes at room temperature. The mixture was then combined with 2.0 ml PBS and aspirated directly through a sheathed H-6000 flow cell, as previously described, with the results illustrated in FIG. 10. A negative control was run in which every step was the same as described above except that the primary antibody was omitted. The results for the control are illustrated in FIG. 11.

These experiments demonstrate that the same excellent separation and reproducibility can be obtained in whole blood as in lymphocyte-enriched suspension. That is to say, two lymphocyte subsets, one of which is labeled, form discrete and separate clusters. The PMNs are to the right of AH threshhold. FIGS. 9 and 11 show that significant numbers of monocytes fall between AL and AH. These are subtracted from the counts from between AL and AH in FIGS. 8 and 10, respectively, to determine the number of stained lymphocytes.

In these whole blood methods, as in Example II, Experiment B (FIG. 6), the early fixation again provides the large and useful gap between unstained and stained lymphocytes.

What is claimed:

1. A flow cytometry method for detecting a lymphocyte population of interest in a heterogeneous whole blood cell suspension containing various classes of leukocytes, and wherein the red blood cells are lysed prior to said measurement, which method comprises:

(a) first reacting said whole blood cell suspension with a first reagent comprising up to about 7.5% formaldehyde and up to about 15% sugar for up to about 10 minutes to fix and stabilize the cells in said whole blood cell suspension;

(b) then incubating said fixed cell suspension of step (a) with a second reagent comprising primary antibodies specific for T lymphocyte or B lymphocyte surface antigens of said lymphocyte population of interest to form a primary antibody-labeled-fixed-lymphocyte population in said cell suspension;

(c) then reacting said primary antibody-labeled-fixed-lymphocyte population of step (b) with an enzyme-ligand-conjugate wherein said ligand is specific for the immunoglobin class of said primary antibodies to form a cell suspension wherein said enzyme-ligand-conjugate is bound to said primary antibody-labeled-fixed-lymphocyte population;

(d) thereafter reacting said cell-suspension of step (c) with at least one composition which reacts with said enzyme to stain said lymphocyte population of interest;

(e) subsequently passing said cell-suspension of step (d) substantially one cell at a time, through a light beam while measuring light scattered and light absorbed by each cell passing therethrough; and (f) discriminating between stained and unstained cells in part on the magnitude of the light scattering and adsorption responses, whereby the stained cells indicate the presence of the lymphocyte population of interest in said heterogeneous whole blood cell suspension.

2. The method of claim 1 further including the step of lysing the red blood cells in said whole blood cell suspension prior to step (a).

3. The method of claim 1 further including the step of lysing the red blood cells in said whole blood cell suspension after step (a).

4. The method of claim 3 further including the step of lysing the red blood cells in said whole blood cell suspension after step (b).

5. The method of claim 4 wherein said primary antibodies of said second reagent of step (b) are monoclonal antibodies.

6. The method of claim 1 wherein said reacting step (c) includes:

(c') incubating said primary antibody-labeled-fixed-lymphocyte population of step (b) with biotinylated secondary antibody specific for said primary antibody to bind to said primary antibody; and (c") thereafter reacting the cell mixture of step (c') with a second enzyme-ligand-conjugate which binds specifically to biotin.

7. The method of claim 6 wherein said biotinylated secondary antibodies are polyclonal antibodies.

8. The method of claim 6 wherein said ligand of said second enzyme ligand conjugate is avidin.

9. The method of claim 8 wherein said enzyme-avidin-conjugate is a peroxidase-avidin.

10. The method of claim 8 wherein said enzyme-avidin-conjugate is an alkaline phosphate-avidin-conjugate.

11. The method of claim 1 wherein said enzyme-ligand-conjugate comprises an avidin-biotin-enzyme-conjugate.

12. The method of claim 11 wherein said enzyme is a peroxidase.

13. The method of claim 11 wherein said enzyme is an alkaline phosphatase.

14. The method of claim 1 wherein said enzyme reacts with a chromogen, and said at least one composition contains a chromogen selected from the group consisting of 3-amino-9-ethylcarbazole and 4-chloro-1-naphthol.

15. The method of claim 1 wherein said sugar is dextrose.

16. A flow cytometry method for detecting a lymphocyte population of interest in a heterogeneous whole blood cell suspension containing various classes of leukocytes, and wherein the red blood cells are lysed prior to said measurement, which method comprises:

(a) first incubating said whole blood cell suspension with a reagent comprising primary antibodies specific for T lymphocyte or a B lymphocyte surface antigens of said lymphocyte population of interest to form a primary antibody-labeled-lymphocyte population in said cell suspension;

(b) then reacting said cell suspension of step (a) with a first reagent comprising up to about 7.5% formaldehyde and up to about 15% sugar for up to about 10 minutes to fix and stabilize the cells in said cell suspension;

(c) then reacting said primary antibody-labeled-fixed-lymphocyte population of step (b) with an enzyme-ligand-conjugate wherein said ligand is specific for the immunoglobin class of said primary antibodies to form a cell suspension wherein said enzyme-ligand-conjugate is bound to said primary antibody-labeled-fixed-lymphocyte population;

(d) thereafter reacting said cell-suspension of step (c) with at least one composition which reacts with said enzyme to stain said lymphocyte population of interest;

(e) subsequently passing said cell-suspension of step (d) substantially one cell at a time, through a light beam while measuring light scattered and light absorbed by each cell passing therethrough; and (f) discriminating between stained and unstained cells in part on the magnitude of the light scattering and adsorption responses, whereby the stained cells indicate the presence of the lymphocyte population of interest in said heterogeneous whole blood cell suspension.

17. The method of claim 16 further including the step of lysing the red blood cells in said whole blood cell suspension prior to step (a).

18. The method of claim 16 further including the step of lysing the red blood cells in said whole blood cell suspension after step (a).

19. The method of claim 18 further including the step of lysing the red blood cells in said whole blood cell suspension after step (b).

20. The method of claim 16 wherein said primary antibodies of said reagent of step (a) are monoclonal antibodies.

21. The method of claim 16 wherein said reacting step (c) includes:

(c') incubating said primary antibody-labeled-fixed-lymphocyte population of step (b) with biotinylated secondary antibody specific for said primary antibody to bind said primary antibody; and (c") thereafter reacting the cell mixture of step (c') with a second enzyme-ligand-conjugate which binds specifically to biotin.

22. The method of claim 21 wherein said biotinylated secondary antibodies are polyclonal antibodies.

23. The method of claim 21 wherein said ligand of said enzyme ligand conjugate is avidin.

24. The method of claim 23 wherein said enzyme-avidin-conjugate is a peroxidase-avidin.

25. The method of claim 23 wherein said enzyme-avidin-conjugate is an alkaline phosphatase-avidin-conjugate.

26. The method of claim 16 wherein said enzyme-ligand-conjugate comprises an avidin-biotin-enzyme-conjugate.

27. The method of claim 24 wherein said enzyme is a peroxidase.

28. The method of claim 26 wherein said enzyme is an alkaline phosphatase.

29. The method of claim 16 wherein said enzyme reacts with a chromogen and said at least one composition comprises a chromogen selected from the group consisting of 3-amino-9-ethylcarbazole and 4-chloro-1-naphthol.

30. The method of claim 16 wherein said sugar is dextrose.

* * * * *